(12) United States Patent
Archak et al.

(10) Patent No.: US 9,355,109 B2
(45) Date of Patent: May 31, 2016

(54) MULTI-TIER CACHING

(75) Inventors: Shrikar Archak, Bangalore (IN); Sagar Dixit, Pune (MH); Richard P. Spillane, Clifton Park, NY (US); Erez Zadok, Stony Brook, NY (US)

(73) Assignee: The Research Foundation For the State University of New York, Albany, NY (US)

( * ) Notice: Subject to any disclaimer, the term of this patent is extended or adjusted under 35 U.S.C. 154(b) by 238 days.

(21) Appl. No.: 13/159,039

(22) Filed: Jun. 13, 2011

(65) Prior Publication Data

US 2012/0072656 A1    Mar. 22, 2012

Related U.S. Application Data

(60) Provisional application No. 61/354,054, filed on Jun. 11, 2010.

(51) Int. Cl.
| | |
|---|---|
| G06F 12/00 | (2006.01) |
| G06F 13/00 | (2006.01) |
| G06F 13/28 | (2006.01) |
| G06F 17/30 | (2006.01) |

(52) U.S. Cl.
CPC ................................. G06F 17/30132 (2013.01)

(58) Field of Classification Search
CPC .............................................. G06F 17/30132
USPC .................................. 711/118, 104, E12.041
See application file for complete search history.

(56) References Cited

U.S. PATENT DOCUMENTS

| | | | | |
|---|---|---|---|---|
| 4,799,152 A | * | 1/1989 | Chuang et al. | |
| 5,530,832 A | * | 6/1996 | So et al. | 711/122 |
| 5,546,559 A | * | 8/1996 | Kyushima et al. | 711/133 |
| 7,707,504 B2 | * | 4/2010 | Quang et al. | 715/735 |
| 7,809,759 B1 | * | 10/2010 | Bruso et al. | 707/797 |
| 8,290,972 B1 | * | 10/2012 | Deshmukh et al. | 707/758 |
| 8,549,518 B1 | * | 10/2013 | Aron | G06F 9/45558 718/1 |
| 8,868,576 B1 | * | 10/2014 | Faibish | G06F 17/30091 707/755 |
| 2002/0073282 A1 | * | 6/2002 | Chauvel et al. | 711/122 |
| 2002/0188821 A1 | * | 12/2002 | Wiens et al. | 711/220 |
| 2003/0028551 A1 | * | 2/2003 | Sutherland | 707/200 |
| 2008/0158958 A1 | * | 7/2008 | Sokolov et al. | 365/185.08 |
| 2009/0006179 A1 | * | 1/2009 | Billingsley et al. | 705/10 |
| 2009/0049234 A1 | * | 2/2009 | Oh et al. | 711/103 |
| 2009/0248987 A1 | * | 10/2009 | Jung et al. | 711/135 |
| 2009/0310412 A1 | * | 12/2009 | Jang et al. | 365/185.11 |
| 2010/0064347 A1 | * | 3/2010 | More et al. | 726/4 |
| 2011/0099342 A1 | * | 4/2011 | Ozdemir | 711/162 |
| 2011/0113194 A1 | * | 5/2011 | Terry et al. | 711/114 |
| 2011/0246503 A1 | * | 10/2011 | Bender et al. | 707/769 |
| 2013/0060922 A1 | * | 3/2013 | Koponen et al. | 709/223 |
| 2014/0280771 A1 | * | 9/2014 | Bosworth et al. | 709/219 |
| 2014/0324821 A1 | * | 10/2014 | Meiyyappan et al. | 707/715 |

* cited by examiner

Primary Examiner — Sheng-Jen Tsai
(74) Attorney, Agent, or Firm — F. Chau & Associates, LLC

(57) ABSTRACT

A method for maintaining an index in multi-tier data structure includes providing a plurality of a storage devices forming the multi-tier data structure, caching an index of key-value pairs across the multi-tier data structure, wherein each of the key-value pairs includes a key, and one of a data value and a data pointer, the key-value pairs stored in the multi-tier data structure, providing a journal for interfacing with the multi-tier data structure, providing a plurality of zone allocators recording which zones of the multi-tier data structure are in used, and providing a plurality of zone managers for controlling access to cache lines of the multi-tier data structure through the journal and zone allocators, wherein each zone manager maintains a header object pointing to data to be stored in an allocated zone.

21 Claims, 6 Drawing Sheets

MULTI-TIER CACHING

CROSS-REFERENCE TO RELATED APPLICATION

This application claims the benefit of U.S. Provisional Application, Ser. No. 61/354,054 filed on Jun. 11, 2010 in the United States Patent and Trademark Office, the contents of which are herein incorporated by reference in its entirety.

STATEMENT REGARDING FEDERALLY SPONSORED RESEARCH

This invention was made with government support under grant number CCF0937854 awarded by the National Science Foundation. The government has certain rights in the invention.

BACKGROUND OF THE INVENTION

1. Technical Field

The present invention relates to key-value storage, indexing, and more particularly to tiered key-value storage and indexing machines comprising a cluster of databases, file systems, or any other storage-stack software.

2. Discussion of Related Art

The volume of index data being generated by network-connected devices is outpacing data storage technologies' speed, capacity, or abilities. Examples of these devices include systems for automatically generating tags, indexing constantly captured video, social-networking services indexing a growing database, and systems that generate large volumes of index data.

Applications that create index data include data-deduplication and provenance systems. Data deduplication is one technology used to compensate for these large databases, where redundant data may be eliminated. Data deduplication relies on indexing to maintain performance levels. Automated provenance collection and indexing are examples of additional growing applications. Automatic provenance collection describes systems that observe processes and data transformations inferring, collecting, and maintaining provenance about them.

Individual machines that form a larger database cluster such as those used by Google's BigTable and Yahoo's Hadoop and HBase perform indexing tasks as well. These machines are referred to as 'Tablet Servers' in the literature. Even database engines such as MySQL's InnoDB, ISAM (Indexed Sequential Access Method), Berkeley DB, and other such key-value stores must perform indexing for traditional RDBMS (relational database management system) workloads. Indexing is being applied to system logs, file metadata, databases, database clusters, media tagging, and more.

In these contexts, and others, indexing is an important component of a variety of platforms and applications.

SUMMARY OF THE INVENTION

According to an embodiment of the present disclosure, a method for maintaining an index in multi-tier data structure includes providing a plurality of storage devices forming the multi-tier data structure, caching a list of key-value pairs stored on one or more tiers of the multi-tier data structure as a plurality of sub-lists according to a caching method, wherein each of the key-value pairs includes a key, and either a data value, a data pointer, the key-value pairs stored in the multi-tier data structure, providing a journal for interfacing with the multi-tier data structure, providing a plurality of block allocators recording which blocks of the multi-tier data structure are in use, and providing a plurality of zone managers for controlling access to blocks within individual tiers of the multi-tier data structure through the journal and block allocators, wherein each zone manager maintains a header object pointing to data to be stored in all allocated blocks.

According to an embodiment of the present disclosure, a method for inserting and retrieving key-value pairs in a machine in communication with multiple storage devices managed in a hierarchy of tiers includes inserting the key-value pairs in the machine and retrieving the key-value pairs from the machine. Inserting the key-value pairs in the machine includes transferring first lists of sorted key-value pairs from a first memory on the machine to a higher (or highest) storage tier of the machine according to a merging method, if there is space available on the higher (or highest) storage tier, transferring second lists from the higher storage tiers to the lower storage tiers within the machine according to the merging method to create space in the higher storage tiers, and transferring third lists from higher machine tiers including the machine to lower machine tiers according to the merging method and conflict resolution algorithm to create space in the higher storage tiers. Retrieving the key-value pairs from the machine includes searching for a first value with a valid key in the first memory on the machine, searching for a second value with the valid key in the highest storage tier of the machine if not present in first memory on the machine, searching for a value with the valid key in the lower storage tiers of the machine if not present on the highest storage tier of the machine, and searching for a value with the valid key in lower machine tiers if not present on higher machine tiers of the machine.

According to an embodiment of the present disclosure, a method for maintaining an index in multi-tier data structure includes managing a plurality of resources within a multi-tier storage system, inserting a copy of at least one of the resources into the multi-tier storage system, detecting, at a selective time, the copy of the at least one resource, and performing a merging method to redistribute the plurality of resources within the multi-tier storage system.

According to an embodiment of the present disclosure, a method for maintaining an index in multi-tier data structure includes managing a plurality of resources within a multi-tier storage system, and performing a merging method to redistribute the plurality of resources within the multi-tier storage system, wherein the merging method is automatically tuned for a workload without disabling the machine.

BRIEF DESCRIPTION OF THE DRAWINGS

Preferred embodiments of the present invention, as well as definitions and meanings of abbreviations, will be described below in more detail, with reference to the accompanying drawings.

DETAILED DESCRIPTION OF EXEMPLARY EMBODIMENTS

According to an embodiment of the present disclosure, a high-throughput, transactional, consistent, multi-tier index and caching system seamlessly spans different storage technologies, exploiting useful properties of each storage technology. Transactional semantics can be full, partial, or none. The multi-tier system, referred to herein as Cascading Hierarchy of Sorted Lists (CHISL), maintains insertion throughputs in excess of a single-node Cassandra installation, a single-node HBase installation, Voldemort, Hypertable, the best-case log-structured index, Berkeley DB, MySQL, XFS, or Ext3 index implementations, and the like, regardless of the storage technology.

CHISL can be used as a storage engine in a single RDBMS, embedded database, a cluster of databases, a local or networked or distributed file system, a deduplication mechanism, and any other implementation in which a key-value store may be used.

Figure 1:
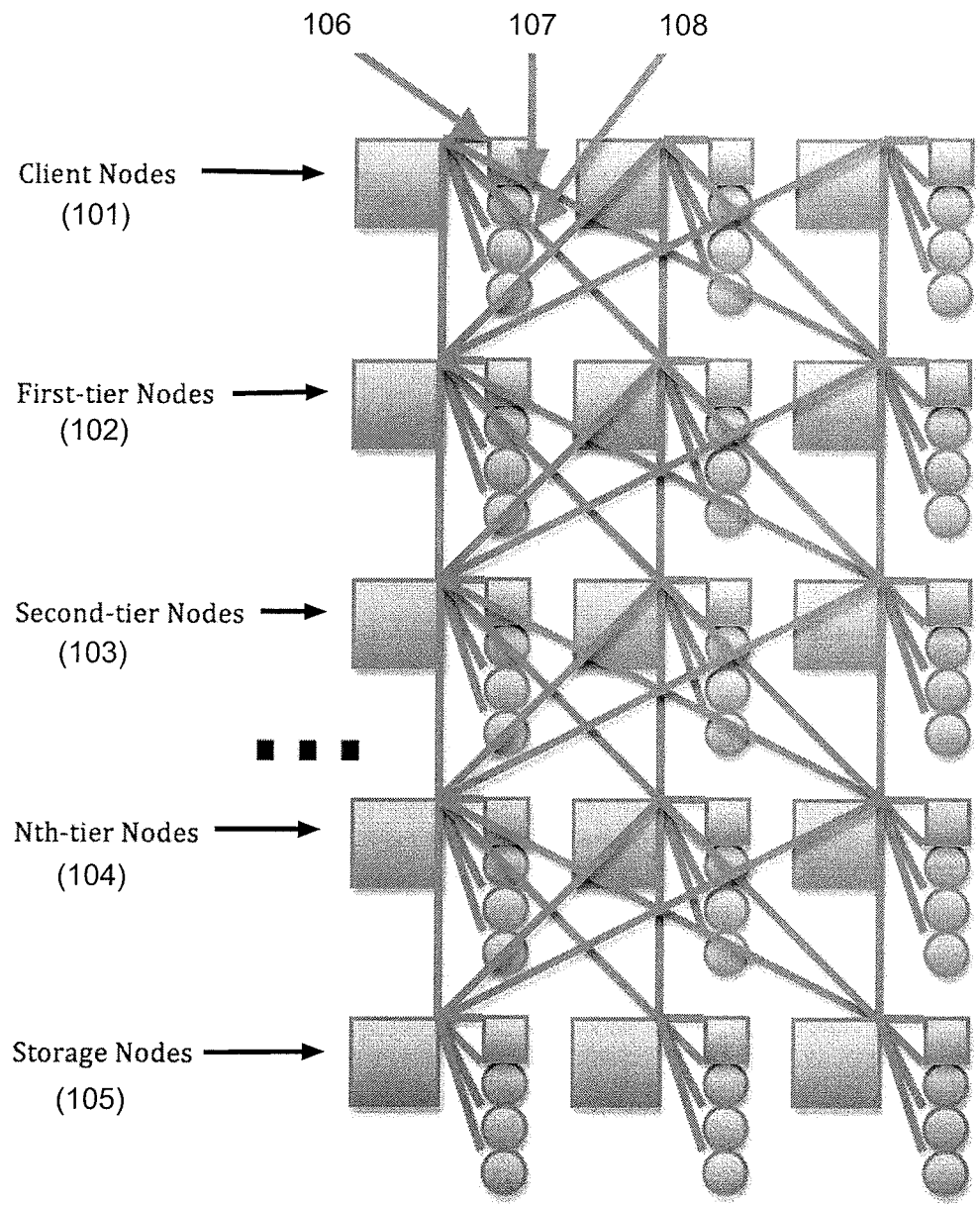
FIG. 1 is a diagram of a tiered storage system according to an embodiment of the present application.

FIG. 1 is an exemplary multi-tier index and caching system including a plurality of different types of nodes. The nodes may be one or more client type 101, one of first through N tier 102-104 or storage type 105. Different tier storage devices are employed at each node type. The tiers may be prioritized, for example, first through third-tier storage devices 106-108. The storage devices may be hosted within one physical machine, or connected by a network. For example, one or more storage tiers may be hosted within a client to a cluster. One or more tiers may be stored at the nodes within the cluster responsible for storing that range of key-value pairs within that key space.

According to an embodiment of the present disclosure, CHISL is an end-to-end transactional indexing storage system. Because Internet data can be stored anywhere from directly attached devices, to near-line ones, to remote clouds, CHISL may scale across arbitrary hierarchies of heterogeneous storage devices and servers, including Flash-based storage. The number of nodes within a single tier, or the number of tiers is not limited.

CHISL insertions may avoid random reads or writes entirely, contributing to its scalability, by utilizing sorted-array merge-trees (SAMT), Cache-Oblivious Look-ahead Array (COLA), other write-optimized indexing technologies, filters such as Bloom filters, etc.

Glossary of Terms

Some terms are used repeatedly throughout the present disclosure and for clarity are defined both when first used, and in this glossary. These definitions apply unless otherwise noted.

Figure 9:
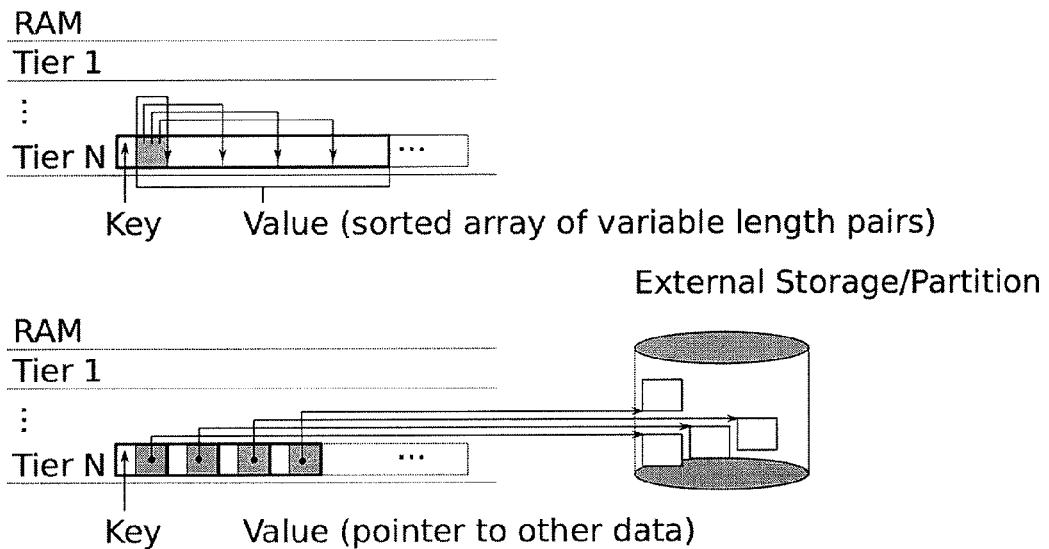
FIG. 9 shows an exemplary CHISL structure employed as a multi-tier column store by storing columns as nested key-value pairs using the CHISL multi-tier hierarchy according to an embodiment of the present application.

Pair: A pair is a variable length key-value pair, where the value can be a nested array of variable length key-value pairs. A value can also be a pointer or an offset to a location in RAM (Random Access Memory) or storage. The key can be sorted with a plurality of sort orders, sorting first by the primary sort ordering. When two keys are considered incomparable or equal by the primary sort ordering, they are sorted by the secondary sort ordering, and so on. Storing an array within a value may be done by first storing a simple secondary index at the beginning of the series of bytes comprising the value, and storing the element key-value pairs within the array. The secondary index may include the offsets to each key, where every $K^{th}$ offset (for a configurable K) also includes that pair's key, or part of key, or K is allowed some variance so that only short keys are chosen. Several configurations of a pair or key-value pair are shown in FIG. 9.

Secondary Index: A secondary index may find a value within an array in a single block or data transfer to the storage device. The secondary index may store one entry for many entries in the array in storage. For example, the offsets of all pairs may be stored within a block at the beginning of the block, and the first pair's key may be stored in the secondary index along with the offset of the block. Further improvements permit efficient mixing of large and small keys. By layering secondary indexes on top of each other a B+-tree index may be created.

Hierarchy: A hierarchy is a structure that stores pointers to all lists within the store. These pointers may be sorted by the age of their lists. For example, if a list A was created before a list B, then the pointer to A will come before B in the hierarchy.

Merging method: Merging methods may use a hierarchy of lists to combine some of these lists together and create a new list based on their age and their size.

Lock resolution method: Lock resolution methods determine what should be done if two pairs have the same value key during a merge. These methods can also be called conflict resolution methods. Common conflict resolution methods include, for example, selecting the pair coming from the younger list, stopping the merge and issuing an error (for example, to retry a transaction), or reporting the conflict in a sorted list of conflicting pairs that can be scanned by a program or machine to determine what to do in the case of each conflict specially.

Caching method: A caching method may be used to determine how to split a list into component sub-lists, and in which tiers to transfer (or not transfer) a sub-list when there is a need to perform a compaction (e.g., to maintain efficient lookup and scan performance, or to create free space). For example a multi-tier read caching method may use 40% of its space to store sub-lists containing only re-inserted reads so as to keep frequently read values in faster storage devices (e.g., Flash, Phase-change Memory, or other memory technology higher in the cache hierarchy). If there is need for space from younger and/or more frequently read sub-lists, older and/or less frequently read sub-lists may be transferred to a storage device lower/slower in the cache hierarchy to make memory available.

Deduplication method: A deduplication method is a specialization of a lock resolution method, where a conflict in keys indicates a duplicate entry, and a message is sent to a block or storage manager to take note of the duplicate for purposes of consistency, performance, efficiency, load balancing, or to reduce unneeded space utilization.

Sequential Optimizations: A exemplary merging method that avoids multiple writes of data that is already sorted, or data that does not require sorting, for example, either because it the data is not complex enough to justify indexing, or the data is large and is always read in whole.

Filtering Method: An extension to the search operation of a merging method where a structure F is maintained for each list and optionally sub-list where unneeded searches are avoided by consulting this structure. This structure may be a compact negative cache. A (compact) negative cache is a compact data structure that supports membership queries on a set. Queries on the negative cache have a small probability of reporting items as being members of the set when they are not. A Bloom filter is an example of a compact negative cache. If a query indicates an item is not a member of the set, the item is not a member of the set. If a list is stored on a device T, the structure F may be stored in a higher tier or faster storage device C. In such a configuration the time spent consulting the structure stored in C is less than the time that would be needed to perform the search in the device T where the list is stored. The structure can be generated when the list or sub-list is created in T, and then either immediately, or at a later time the generated structure can be transferred to the faster device C.

TSSL/Pair Store: The Tablet Server Storage Layer (TSSL) is a database or database-like storage software which may be installed on every node in a cluster of databases. The TSSL controls a plurality of pair stores: data structures designed to store key-value pairs or pairs. CHISL is a suitable pair store for a TSSL, and can be used as a component of a column store or any other database store.

SSTable: Another name for a list stored on a storage device.

Memtable: Another name for the $C_0$ buffer stored in a fast storage device such as RAM or some other suitable memory technology.

1. Merging Method Adaptations Overview and Analysis

According to an embodiment of the present disclosure, a multi-tier storage hierarchy may be implemented having an arbitrary merging method and caching method, with a lock resolution, duplicate management, sequential optimizations, and dynamic reconfiguration method. Exemplary merging methods are described in this section. Exemplary embodiments of a CHISL multi-tier method are described herein. Further, implementations of a merging method compatible with embodiments of the present disclosure, extending a SAMT merging method using a CHISL multi-tier method, are described.

According to an embodiment of the present disclosure, a merging method may be tuned or selected for a level of insertion ingestion. The merging method may be automatically changed to merge more frequently in order to maintain fewer lists, wherein lookups need only query a small number of lists, at the expense of more time spent merging and therefore a lower insertion throughput. The tuning or selection of a merging method is complementary to embodiments described herein and can be used to create a flexible multi-tier storage system capable of managing duplicate resources, caching sub-lists in different storage tiers according to the caching method, and processing either high volumes of insertions while maintaining efficient and bounded lookup and scan performance, or vice verse, according to workload conditions.

According to an embodiment of the present disclosure, a position of each list may be stored within the multi-tier storage in a fast storage device, for example the machine's RAM. Alternatively, each list's position within the multi-tier storage hierarchy may be determined before a merge is performed according to the merging method. Regardless of whether the hierarchy is stored continuously, or only determined selectively, all such machines are embodiments of the present disclosure.

To perform an insertion of key-value pairs with potentially completely random values, merging methods may be employed where key-value pairs are sorted in RAM, and merged with sorted lists already on a storage device. By selecting a number of lists to merge together when transferring key-value pairs from RAM to storage, based on age, the overall time spent inserting many key-value pairs may be reduced. There are several methods by which a sorted list of the most recently inserted key-value pairs in RAM can be merged with sorted lists already in storage, called merging methods.

According to an embodiment of the present disclosure, list merging may be performed in connection with a plurality of storage devices with different random and serial read and write throughputs. These storage devices may be connected to one or more machines. According to an embodiment of the present disclosure, lists may be stored as sub-lists that store different kinds of information. For example entries that were inserted to speed lookups may be separated from entries that were inserted to update existing key-value pairs. The separation of lists into sub-lists permits managing methods to keep recently read information in more efficient storage devices, while recently inserted information is transferred to another storage device, for example one with comparable cost (e.g., monetary) that is slower but larger. Further, the separation of lists may allow a device to effectively store structured data typically stored in an RDBMS, database engine, or database cluster node in a cache hierarchy of storage devices, where all devices are comparable in cost, but larger storage devices are slower to access. In addition, the separation of lists may allow devices to store the same amount of structured data, and to speed up workloads that access a portion of this data too large to fit in RAM, small enough to fit in a storage device slower and larger than RAM, and faster and smaller than disk or a device that can store more structured data as compared to other devices when cost is comparable.

Exemplary merging method adaptations described herein can store which lists are to be merged based on age, frequency of use, or other criteria in RAM at all times, or alternatively can determine which lists are to be merged according to this criteria before merging them into a larger list to be transferred to some storage tier in the multi-tier hierarchy. The information used to determine which lists are to be merged and in what order is called a hierarchy. Whether an adaptation constructs its hierarchy before the merge or maintains its hierarchy continuously is an implementation detail and does not alter an adaptation of the present disclosure.

Amortized versions of two alternate merging methods, specifically the COLA Merging Method Adaptation and the SAMT Merging Method Adaptation are described herein. Techniques described herein from adapting these merging methods to utilize a multi-tier structure according to an embodiment of the present disclosure are applicable to other merging methods including deamortized versions. The specific method by which an adaptation is performed is an implementation detail. One exemplary technique to achieve deamortization is to perform a portion of a next set of merges during each insertion. This can be achieved by performing merges asynchronously in the storage tiers while using a timer to throttle insertions into $C_0$, or by synchronously performing a portion of the next scheduled merge before each insertion into $C_0$.

Metric of Abstract Analysis

According to an embodiment of the present disclosure, a multi-tier storage hierarchy may be scaled. Current systems utilize merging methods that are insensitive to the problems faced by a multi-tier hierarchy. Two existing compaction methods are discussed herein, and in Section 2, extensions are described for applications to a multi-tier regime according to an embodiment of the present disclosure. Compaction performance of the methods is analyzed using the Disk-Access Model (DAM) for cost. DAM divides the system into a memory M and storage S. The unit of transfer from S to M is a block of b bytes. Operations and manipulations of data in M are at no cost. Blocks transferred either from M to S or from S to M cost 1. For the remainder of this analysis, B=b/<size of key-value pair> is used instead of b. This means each data structure is penalized 1 unit for reading or writing a key-value pair to a random location in storage S, or is penalized 1 unit for reading or writing a series of B key-value pairs to a random location in storage S.

COLA Merging Method Adaptation

HBase is a variation of the Cache-Oblivious Lookahead Array (R-COLA). The R-COLA supports increasingly more read-optimized configurations as its R parameter is increased. HBase sets R=3, which is optimal in practice for the R-COLA, and the particular HBase configuration may be referred to as a 3-COLA. FIG. 3C, panel 1, shows an R-COLA including $\lceil \log_R (N) \rceil$ arrays of exponentially increasing size, stored contiguously ($C_0$ through $C_3$). In this example, R=3. $C_1$ through $C_3$ on storage 304 can be thought of as three lists (e.g., SSTables), and $C_0$ in RAM 305 can be thought of as a buffer in a fast storage device such as RAM (memtable). The memtable is a write-back cache storing data that may be looked up by key. When the memtable is serialized to disk 304 and turned into an SSTable, the R-COLA checks to see if level 0 is full. If level 0 is not full, it performs a merging compaction on level 0, on all adjacent subsequent arrays that are also full, and on the first non-full level, into that same level. In FIG. 3C panel 2, $C_0$ through $C_3$ are merged into $C_3$; after the merge, the original contents of $C_3$ have been written twice to $C_3$. Each level can tolerate R−1 merges before it needs to be included in the merge into the level beneath it. This means that every pair is written R−1 times to each level. $C_0$ can be serialized to a slot in $C_1$. As every element visits each level once, and merges are done serially, $\log_K(N)$ disk transfers are performed per insertion. Because there are K slots per level, and $\log_K(N)$ levels, $K \ast \log_K(N)$ disk transfers are performs per lookup. The cost of lookup with the SAMT is the same for K=2 and K=4, but K=4 provides faster insertions. K=4 may be used as a default.

SAMT Merging Method Adaptation

The R-COLA used by HBase has faster lookups and slower insertions by increasing R. CHISL and Cassandra may be configured to provide faster insertions and slower lookups by organizing compactions differently. The structure adopted by Cassandra's TSSL and CHISL is referred to as a Sorted Array Merge Tree (SAMT). As shown in FIG. 3C, panel 2, the SAMT stores K lists, or slots on a plurality of levels $C_0$-$C_3$. The memtable or $C_0$ can be flushed K times before a compaction is performed. The slots in $C_1$ are merged into a slot in $C_2$. In the example depicted, a cascade of compactions is performed: the slots in $C_2$ are merged into a slot in $C_3$, so that the slots in $C_1$ can be merged into a slot in $C_2$ and the memtable can be flushed to $C_1$.

Comparison of COLA and SAMT

It should be understood that panels 1 (HBase 3-COLA) and 2 (Cassandra SAMT) of FIG. 3C are not multi-tier structures. Although the HBase 3-COLA method permits more aggressive merging during insertion to decrease lookup latency by increasing R, it may not favor insertions beyond its default configuration. This permits faster scan performance on disk, but for 64 byte or larger keys, random lookup performance is already optimal for the default configuration. This is because for most lookups, Bloom filters on each SSTable avoid all $\log_R(N)$ SSTables except the one which contains the sought after pair. Furthermore, on Flash SSD the 3-COLA is less optimal, as even the seeking incurred from scanning is mitigated by the Flash SSD's obliviousness toward random and serial reads. Conversely, the SAMT can be configured to further favor insertions by increasing K, while maintaining lookup performance on Flash SSD and disk by using Bloom filters, and maintaining scan performance on Flash SSD. Although Bloom filters defray the cost of unneeded lookups in SSTables, as the number of filters increases, the total effectiveness of the approach may decrease. When performing a lookup in the SAMT with a Bloom filter on each SSTable, the probability of having to perform an unneeded lookup in some SSTable is $1-(1-f)^{NB}$ where NB is the number of Bloom filters, and f is the false positive rate of each filter. This probability is about equal to f*NB for small values of f Bloom filters may be effective as long as the number of SSTables remains finite. For a Bloom filter filtering method, having the number of each tree/column-family being less than about 40 is sufficient, other filtering methods may have different values depending on their space efficiency for higher false positive rates.

2. Exemplary Design and Implementation

Figure 7:
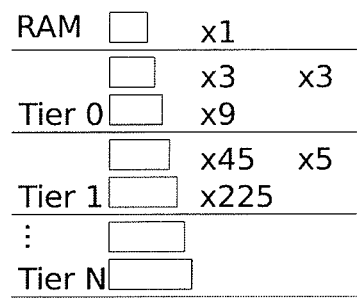
FIG. 7 is an exemplary CHISL configuration having one or more slots or lists per level or cache line according to an embodiment of the present application.

CHISL utilizes several extensions to the SAMT (discussed in Section 3). As shown in FIG. 3C panels 3 and 4, CHISL supports storage device specific optimizations at each tier, e.g., RAM, SSD and Disk. CHISL migrates recently written and read data between tiers to improve both insertion and lookup throughput and permit caching in storage tiers larger than RAM. Referring to FIG. 7, CHISL may be configured to have different numbers of slots or lists per level or cache lines according to an embodiment of the present application.

TSSL efficiency is related to overall cluster efficiency. CHISL extends the scan cache and buffer cache architecture used by existing TSSLs. CHISL avoids the need to maintain a buffer cache while avoiding common memory-mapping (MMAP) overheads. CHISL further exploits Bloom filters so that they have equal or more space in RAM than the scan cache. Although Web-service MapReduce workloads do not typically require more than atomic insertions, parallel DBMS (Database Management System) architectures and many scientific workloads use more substantial transactional semantics. CHISL introduces an optional transactional architecture that allows clients to commit transactions as either durable or non-durable. Durable transactions exploit group-commit as in other TSSL architectures. CHISL also allows non-durable transactions, and these can avoid writing to the journal completely for heavy insertion workloads without compromising recoverability. In addition, CHISL provides the infrastructure to support transactions that can perform multiple reads and writes atomically and with full isolation.

Exemplary CHISL Method

A CHISL multi-tier method (CHISL method) permits the modification of a merging, caching, lock resolution, duplicate management, sequential optimization, filtering method, and dynamic reconfiguration method to operate within a multi-tier storage environment, where multiple devices are grouped into multiple tiers.

There may be many such groupings for the same set of devices. An example is shown in FIG. 1, where the CHISL method groups devices (Nodes) with similar random and serial read and write storage characteristics into tiers. Nodes within a tier are responsible for merging lists of data sent to that node from one or more nodes in another tier, and then at some point transferring these lists to one or more nodes in another tier. The example in FIG. 1 shows one grouping of machines where one or more nodes of the Client type transfer lists to one or more nodes of the First type. At some point these lists along with subsequent lists are merged together according to the merging method, and according to the caching and merging method a time is chosen where these lists are then transferred to one or more nodes of the Second-tier type. The same decision is repeatedly made and the data percolates whole or in part down (from Client to Storage) through the tiers. Although the example in FIG. 1 shows only three nodes within each tier, it is explicitly noted that any number of nodes may belong to a single tier, and there may be any number of tiers. Furthermore, the channels by which data is sent from one node to another may be any medium, either an Ethernet device, or any WAN/LAN networking medium suitable for a bus between devices not within close proximity of each other, or a bus such as SCSI, SATA, or any medium suitable for a bus between devices within close proximity of each other.

Figure 4:
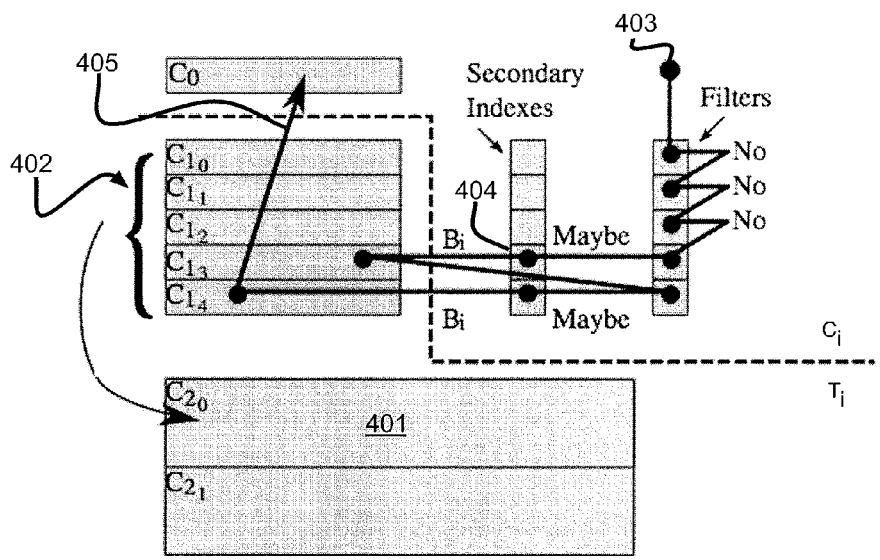
FIG. 4 shows an exemplary SAMT with multiple slots, secondary indexes, and filters according to an embodiment of the present application.

Retrieval of data from CHISL begins with a client or user selecting a pair to lookup or scan. According to a lock resolution method, the user may be required to notify one, some, or all of the nodes of this access. As shown in FIG. 4, each node organizes its memory in order of most randomly accessible to least randomly accessible. When comparing storage devices within different tiers, and which may exist either within the same machine or on different machines, one tier is more randomly accessible than the other. This more randomly accessible tier is the cache for the less randomly accessible tier. For example, in the two-tier example of FIG. 4, a slot in a lower level 401 (the less randomly accessible tier) needs to be able to contain all the slots 402 in the lowest level of the next higher level (the more randomly accessible tier). The cache tier C for some other tier T may contain secondary indexes and space-efficient filters. If they exist, these secondary indexes and filters are consulted on tier C before searching for the pair in the tier T. If the pair can be proven to not exist by the filters, then lookup may stop, otherwise if the exact key of the pair is not known or the existence of the pair is still in question a lookup may proceed with the optional locational information provided by the secondary index in C. If the pair is not found in T, the search proceeds to other nodes. Searches of nodes can be parallelized across tiers, and can simultaneously be performed in order of the fastest tiers to slowest tiers, in this way, it is more likely that the C tier for some T tier will be more quickly located and accessed, thus possibly eliminating the need to consult the slower T tier at all.

To improve read throughput, when the work-set size is small enough to fit in a RAM, e.g., the C tier, using RAM as a cache, e.g., the T tier, may provide the improved performance. A filter may be used on each of the slots in levels too large to fit in a given tier, e.g., C. In an exemplary lookup in 403 of FIG. 4, no key is found in $C_0$. Thereafter, filters are sequentially checked. In the example, $C_{1.0}$'s filter reports "No," as does $C_{1.1}$ and $C_{1.2}$'s, and $C_{1.3}$'s reports "Maybe," and the block is inspected using its' corresponding secondary index 404. In the example, the key is not found and the method continues to $C_{1.4}$, and finding the key there, the key is copied back into $C_0$ for reading 405. For medium sized (e.g., 128 byte) key-value pairs, filters may enable 1 I/O per lookup, despite being write-optimized. Secondary indexes consume an equivalent amount of resources as the immediate parents of the leaf nodes in a B-Tree, which are typically cached in RAM. As seen in FIG. 4, a filtering method may be used to avoid searches in lists where the sought after pair is not present. Typically the structures consulted by this method would be stored in the faster storage device $C_i$, and the lists for which searches are avoided would be stored in storage device $T_i$. In some embodiments of the filtering method, the structures that must be consulted would likely be generated at the time the lists are first constructed by the merging method. Either the structures would be created in corresponding $C_i$ simultaneously, or would be transferred there with a sequential read and write at some later time, determined by the filtering method. The storage device $C_i$ in which these structures are stored need not be the highest or fastest such storage device, typically as long as $C_i$ is faster than the corresponding $T_i$, this would be sufficient.

Figure 8:
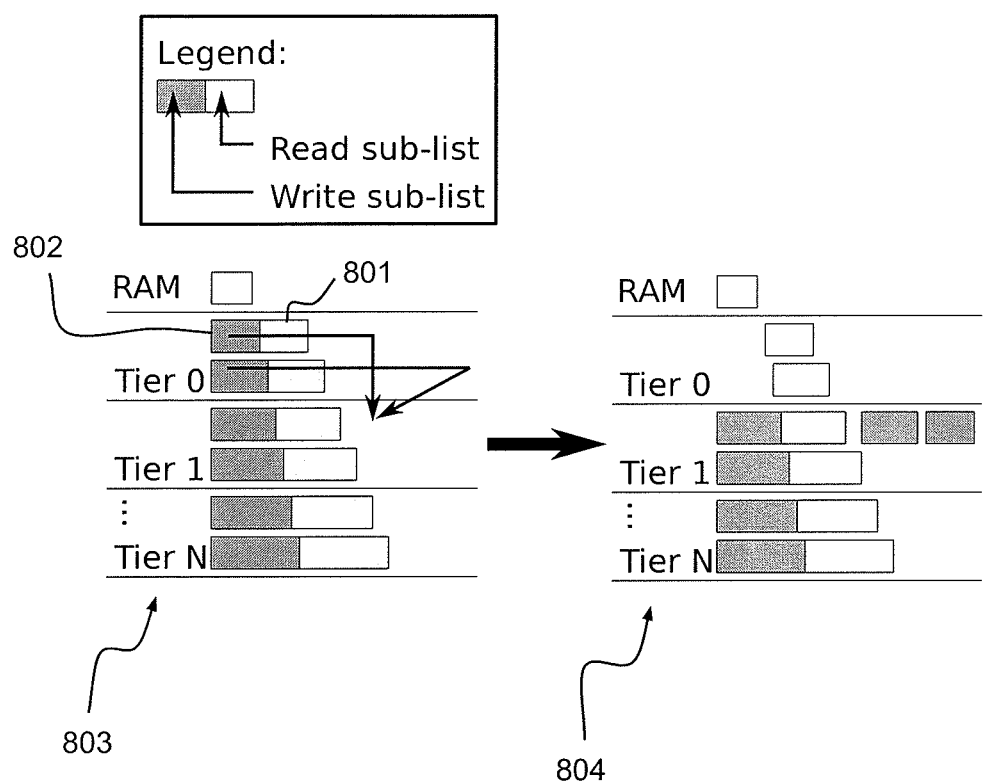
FIG. 8 shows an exemplary merge and cache method in an exemplary CHISL implementation according to an embodiment of the present application.

Insertion of data into CHISL begins with a client or user selecting a pair to insert, modify, or read. According to a lock resolution method, the user may be required to notify one, some, or all of the nodes that the pair is being accessed. Space within each node may be divided according to the caching method, for example as shown in FIG. 8, into read caching space and write caching space. FIG. 8 shows an exemplary merge and cache method using CHISL to retain a sub-list 801 of a list that contains frequently read data in a relative high tier (tier 0), while transferring a sub-list 802 of the same list that contains writes (e.g., insertions, updates, and deletions) to a relatively low tier (tier 1). A merge method may be applied to the structure 803 to move a write sub-list 802, while the cache method will leave the read sub-list 801 in place. The merge and cache method result in the structure 804, wherein the write sub-lists have been moved to a lower tier (tier 1).

The allotment may change over time as performance requirements change depending on the workload according to the dynamic reorganization method. If there is not enough space to accommodate the potentially newly updated or read pair, then according to the merging method, the lists occupying the memory are transferred to another node according to the merging method. If there is more than one list being transferred, none, some, or all of these lists may be merged at the time of transfer. The number of lists merged is determined by the merging method, the sequential optimization method, and the dynamic reorganization method, which examine the number, the size, the complexity of the list's secondary index and filters, and the desired insertion, update, delete, scan, and lookup performance of the workload and/or user. If the determination to merge is made, then during merge, a lock resolution and deduplication method are utilized to determine how to handle pairs with conflicting keys, where keys conflict if they are incomparable or are equal in value. At this point a lock resolution method may stop the merge and alert a conflict resolution authority, such as an automated process, or a user by issuing a human understandable error. At this same point a deduplication method may notify a duplicate pair manager that two pairs with potentially duplicate key values exist, and this entity may decide to remove the duplicate to save space, or move it physically to another node for performance, reliability, security, or any other reason.

Once enough space has been created to accommodate the new pair(s) by transferring and possibly merging already present lists, they are transferred from the user's or client's memory to the node and form a new list or modify an existing list. According to a caching method, not all lists may be transferred at this time. For example, in FIG. 8, the list is broken into a read and write sub-lists, where only the write sub-lists are transferred to another node, and the read sub-lists remain unless further space is needed, or performance or security requirements change according to the dynamic reorganization method.

Figure 10:
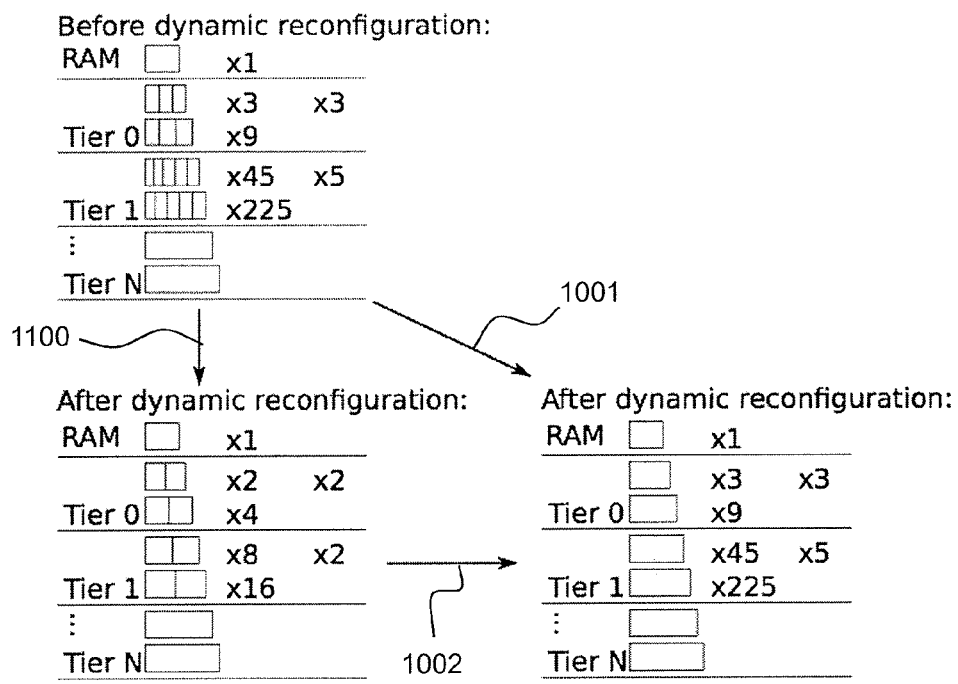
FIG. 10 shows exemplary CHISL reconfigurations, dynamically shifting from a write-optimized merging method to a more read-optimized merging method according to an embodiment of the present application.

The dynamic reorganization method may alter the thresholds used to determine if a merge or list transferal is required as shown in FIG. 10. For example, the number of slots/lists in each tier can be reconfigured to induce more merging during regular operation of the merging method, deamortizing read optimization across multiple evictions/transfers 1000 or lists on the same level (slots) can be merged together for aggressive read optimization 1001 or 1002.

Figure 2:
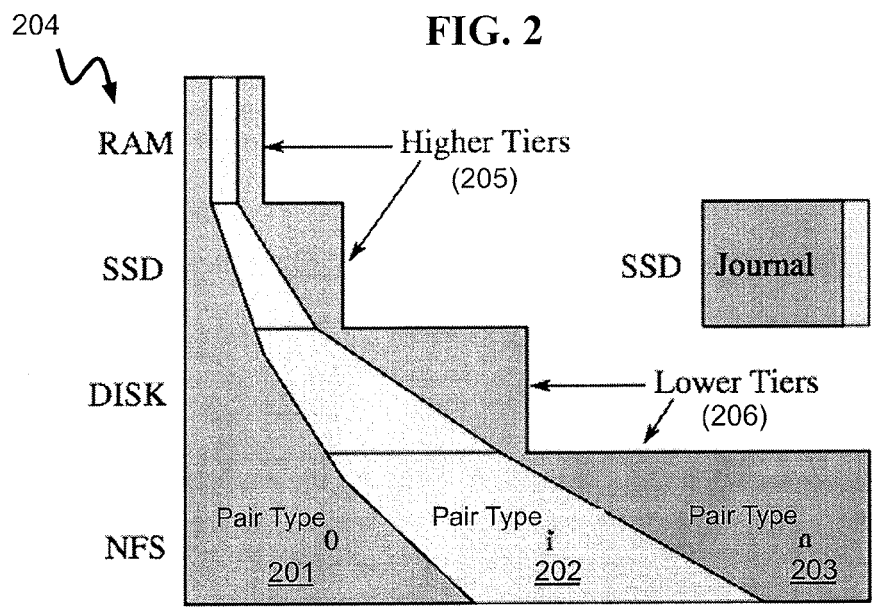
FIG. 2 is an exemplary CHISL multi-tier system according to an embodiment of the present application.

As shown in FIG. 2, multiple pair types (201-203) can be stored across a series of devices 204 from higher tiers 205 to lower tiers 206. As shown in FIG. 9, column and row storage, along with other localization and data locality optimizations may be achieved by configuration of the pairs used within a pair type. For example, CHISL may be employed as a multi-tier column store by storing columns as nested key-value pairs using the CHISL multi-tier hierarchy.

A properly suitable sequential optimization method can be used to avoid re-writing portions of lists during a merge by identifying which pair types or arrays within pairs need to be sorted, and which do not, along with performance requirements for scans and lookups.

Figures 3A, 3B:
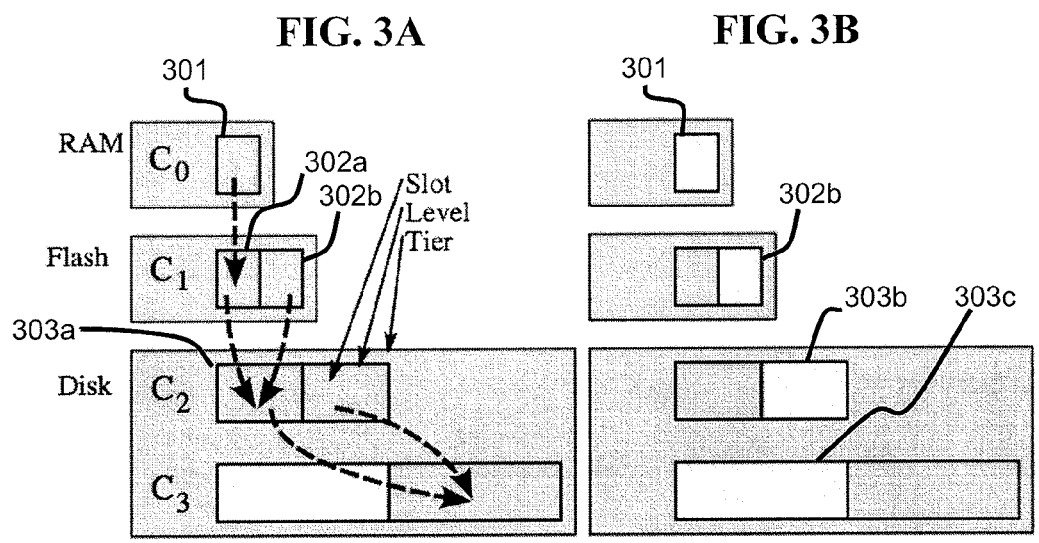
FIGS. 3A-C show exemplary merging methods according to an embodiment of the present application.
Figure 3C:
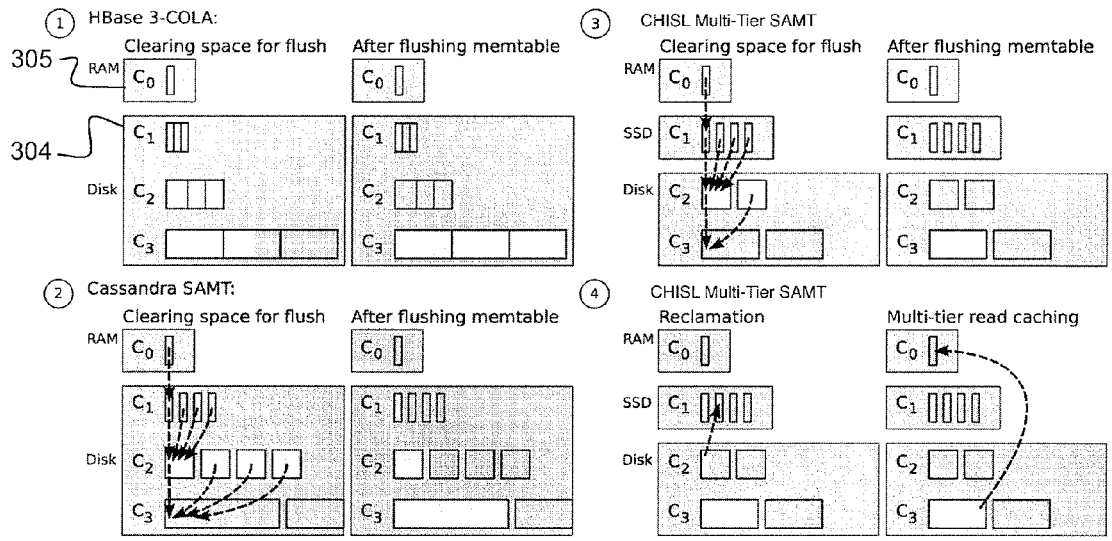

FIGS. 3A-B show a configuration with a single device, organizing its storage into three tiers, where the bus is a SATA and memory bus connection, where the number of lists within a tier is configured at two, and one in the highest tier (RAM in this case).

As seen in FIG. 3A, the key-value store is divided into an in-RAM cache and an on-storage set of sorted lists. The cache includes a red-black tree of pairs. The on-storage component includes a series of levels, where each level holds two or more slots. A slot is a sorted array of pairs. The key-value store uses red-black trees as a cache structure, and when these caches are full, it will flush their contents in large serial writes to the slots and levels of the on-storage component. Throughout operation, a merging regiment on these slots and levels is used to maintain high insert, delete, and update throughput.

Operations may be categorized as either reads or writes. Reads include: (1) finding an exact value if it exists or find-exact, and (2) range queries. Writes include: (1) insert, (2) delete, and (3) update.

Write: Pairs can be inserted between existing pairs. Updates and deletes change the value of a pair or remove it entirely. After elements are deleted, new elements can be inserted again. Inserts fail with an ENOSPC error (no space left on device) when the allotted space is full.

Referring to FIG. 3A, new key-value pairs are inserted into the cache in RAM, called $C_0$ 301. When there is no more RAM for insertions, $C_0$ flushes all key-value pairs in sorted order as a contiguous serial write to an empty slot in $C_1$, which is then marked full. $C_1$ has two slots 302a and 302b, each of which can hold as much data as $C_0$; this relationship holds for each $C_i$ and $C_i-1$ with the exception of a lowest-order slot (explained below). When a cache line $C_i-1$ has no empty slots, SAMT merges the contents of both of its slots into one of the slots in ci 303a. It then marks the slot in ci full and both slots of $C_i-1$ free. This may result in a cascading merge; FIG. 3A shows a multi-tiered cache before cascading and FIG. 3B shows a multi-tiered cache after cascading wherein portions of cache, e.g., 301, 302b, 303b, and 303c are flushed.

Figure 5:
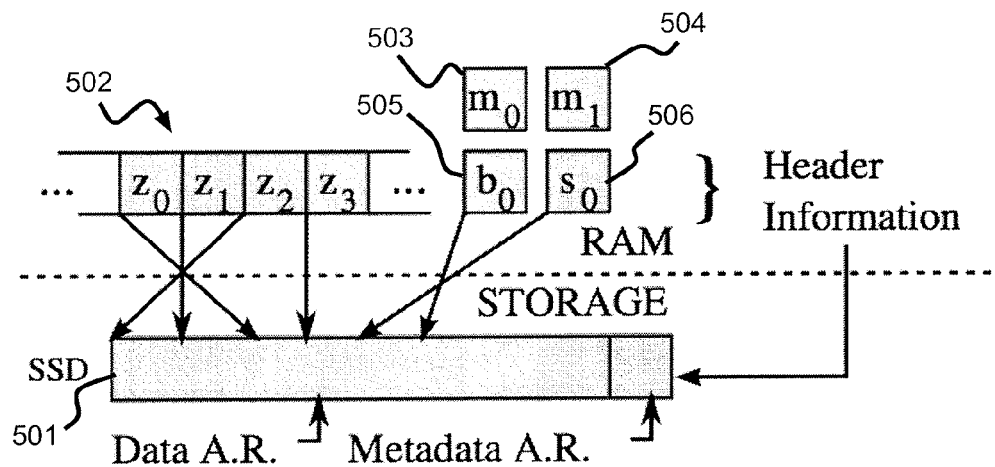
FIG. 5 shows SAMT tier header and block allocators according to an embodiment of the present application.

For each tier that a particular key-value pair occupies, CHISL maintains a tier header, depicted in FIG. 5, to manage metadata associated with the portion of a key-value pair structure within that tier. Each slot in a key-value pair structure is divided into blocks. By representing slots as a series of blocks, unused space from partially filled slots may be re-used, and multiple snapshots of the key-value pair structure may be stored to simplify a transactional implementation. The size of the blocks may be set to reduce or avoid fragmentation, e.g., 1 GB.

FIG. 5 shows a portion of a tier header corresponding to a single slot 501 residing on an SSD. The blocks 502 (z0 through z3) are mapped out of order to the slot. The blocks size ensures good serial write performance. The offsets of blocks are in turn managed by a block allocator. The partition of storage that each block allocator manages is called its allocation region. Block allocators maintain a bitmap of which blocks are free or not. For example, for 1 GB blocks, a 4 KB bitmap can represent 32 TB worth of blocks, and a bitmap will flush quickly to the journal and consume little memory. In FIG. 5 there are two block allocators 503 and 504 controlling this SSD ($m_0$ and $m_1$). Block allocator $m_0$ allocates 1 GB blocks for slot blocks from a data allocation region (Data A.R.). Block allocator $m_1$ allocates 8 MB blocks to store tier header information and both block allocators' bitmaps (Metadata A.R.). Larger blocks avoid seeking during list merges. Small blocks avoid wasting space for storing metadata. The filter and secondary index are resident in some fast storage device (could be RAM, but not necessarily), and may also be stored on disk to be recoverable after a crash. The offsets of the locations of the filter and secondary index are maintained by the header in block $b_0$ 505 and block $s_0$ 506, respectively.

Exemplary SAMT Multi-Tier Extensions

CHISL may extend the SAMT merging method in multiple ways. For example, (1) Client reads can be optionally re-inserted to keep recently read (hot) data in faster tiers (e.g., a Flash SSD). (2) Lists of recently inserted data are automatically promoted into faster tiers if they fit. (3) Different tiers can have different values of K (the number of slots in each level.

According to an embodiment of the present disclosure, a SAMT the Multi-tier SAMT or MTSAMT is described. The exemplary implementation includes support for full deletion, variable-length keys and values, and allows the logical layer to specify whatever format, bits, or timestamps deemed necessary by the logical layer, as other TSSLs do.

Exemplary Re-Insertion Caching

Whenever a pair is inserted, updated, deleted, or read, the $C_0$ (fastest) cache may be updated. The cache may be configured to hold a preset number of pairs. When a pair is inserted or updated, it is marked DIRTY, and the number of pairs in the cache is increased. Similarly, after a key is read into the $C_0$ cache, it is marked RD_CACHED, and the number of pairs is increased. Once a pre-set limit is met, the cache evicts into the MTSAMT structure using the merging process depicted in FIG. 3C panel 3. By including RD_CACHED pairs in this eviction as regular updates, we can answer future reads from $C_1$ rather than a slower lower level. However, if the key-value pairs are large, this can consume additional write bandwidth. This feature is desirable when the working-set is too large for $C_0$ (RAM) but small enough to fit in a fast-enough device residing at one of the next several levels (e.g., $C_1$ and $C_2$ on Flash SSD). Alternatively, this feature can be disabled for workloads where saving the cost of reading an average pair is not worth the additional insertion overhead, such as when we are not in a multi-tier scenario. All RD_CACHED values are omitted during a major compaction, and RD_CACHED values are omitted during a merging compaction if another pair with the same key can be emitted instead. Therefore, no additional space is used by inserting RD_CACHED pairs. When scanning through trees (MTSAMTs), if read caching is enabled, the scanner inserts scanned values into the cache, and marks them as RD_CACHED. Experimentally, we found that randomly reading larger tuples (>4096 KB) can make effective use of a Flash SSD tier; however, for smaller tuples (<64 B) the time taken to warm the Flash SSD tier with reads is dominated by the slower random read throughput of the magnetic disk in the tier below. By allowing scans to cache read tuples, applications can exploit application-specific locality to pre-fetch pairs within the same or adjacent rows whose contents are likely to be later read. Evictions of read-cached pairs can clear out a Flash SSD cache if those same pairs are not intelligently brought back into the higher tier they were evicted from after a cross-tier merging compaction. In FIG. 3C panel 4, evicted pairs are copied back into the tier they were evicted from. This is called reclamation, and it allows SSTables, including read-cached pairs, that were evicted to magnetic disks (or other lower-tier devices) to be automatically copied back into the Flash SSD tier if they can fit.

Exemplary Sub-List Optimization

Read-cached values need not be stored in the same lists as other pairs, but can instead be segregated into a separate list which is created at the same time, but holds only read-cached values. When a merging compaction takes place, and lists from one tier are merged together, and the result is written to another or lower tier, the read-cached list can remain where it is, or can be moved to a higher or faster tier. This allows an operator of the machine or system to configure a proportion of faster storage devices to use an allotted space for caching. Without separating reads into sub-lists, they would be carried downward to another tier during the merge. By leaving the read-cached pairs in place, and only transferring the inserted pairs, reads can still be serviced at the speed of the faster storage device.

Exemplary Space Management and Reclamation

An MTSAMT may be designed for so that more frequently accessed lists would be located at higher levels, or at $C_i$ for the smallest i possible. After a merge, the resulting list may be smaller than the slot it was merged into because of resolved deletes and updates. If the resultant list can fit into one of the higher (and faster) slots from which it was merged (which are now clear), then it may be moved upward, along with any other slots at the same level that can also fit. This process is called reclamation.

In the example in FIG. 3C, the result of the merging compaction in panel 4 is small enough to fit into the two (half of four) available slots in $C_1$, and specifically in this example requires only one slot. If multiple slots were required, the SSTable would be broken up into several smaller SSTables. This is possible because CHISL manages blocks in the underlying storage device directly, rather than treating SSTables as entire files on the file system, which allows for this kind of optimization. Reclamation across levels within the same tier is inexpensive, as this includes moving SSTable blocks by adjusting pointers to the block, rather than copying them across devices. If these rules are obeyed, then partially filled slots may be guaranteed to always move upward, eliminating the possibility that small lists of pairs remain stuck in lower and slower levels. The exemplary MTSAMT implementation has been designed for throughput. The exemplary design considers space on storage with high latency and high read/write throughput characteristics (e.g., disk) to be cheaper than other hardware (e.g., RAM or Flash SSD). CHISL can operate optimally until ½ of total storage is consumed; after that, performance degrades gradually until the entire volume is full, save a small amount of reserve space (usually 5% of the storage device). Such space-time trade-offs are common in storage systems, such as HBase, Cassandra, and even Flash SSD devices.

At this point, only deletes and updates may be accepted. These operations are processed by performing the equivalent of a major compaction: if there is not enough space to perform a merging compaction into the first free slot, then an in-place compaction of all levels in the MTSAMT is performed using the CHISL's reserve space. As tuples are deleted, space is reclaimed, freeing it for more merging compactions that intersperse major compactions until ½ of total storage is again free; at that point, only merging compactions need be performed, regaining the original optimal insertion throughput.

To exploit decoupling, compaction-based systems such as CHISL have some overhead to maintain optimal insertion throughput in the steady state. Without this space, their throughput will degrade.

Exemplary Committing and Stacked Caching

The exemplary MTSAMT extends the SAMT to operate efficiently in a multi-tier environment. In addition to efficient compaction, reclamation, and caching as discussed above, the efficiency of the memtable or $C_0$ as well as how efficiently it can be serialized to storage as an SSTable is also discussed. The architecture of a transaction manager and caching infrastructure affects insertion throughput for small key-value pairs (<1 KB). CHISL's architecture is mindful of cache efficiency, while supporting new transactional features (asynchronous commits) and complex multi-operation transactions.

Exemplary Cache Stacking

The transactional design of CHISL may be implemented in terms of CHISL's concise cache-stacking feature. CHISL maintains a memtable to store key-value pairs. CHISL uses a red-black tree with an LRU implementation, and DIRTY flags for each pair. An instance of this cache for caching pairs in a particular column family or tree is called a scan cache. Unlike other TSSL architectures, this scan cache can be stacked on top of another cache holding pairs from the same tree or MTSAMT. In this scenario the cache on top or the upper cache evicts into the lower cache when it becomes full by locking the lower cache and moving its pairs down into the lower cache. In addition to the memtable cache, like other TSSLs, CHISL may use a buffer cache. The buffer cache need not fully implement a user-level buffer cache.

Exemplary Buffer Caching.

According to an embodiment of the present disclosure, on operating system (OS) kernel, such as Linux, may be used for all caching of pages read from zones by mmap-ing (maping files or devices into memory) storage in 1 GB slabs, or chunks. This simplifies a design implementation by avoiding implementing a buffer cache. 64-bit machines' address spaces are sufficiently large and the cost of a random read input/output (I/O) exceeds the time spent on a TLB miss. Serial writes may be used on a map, incurring reads as the underlying operating system kernel reads the page into the cache, even on a write fault. This may cause overhead on serial writes due to the additional reads. To avoid this problem, an operation such as PWRITE may be used during merges, compactions, and serializations, wherein the affected mapping may be invalidated using, for example, MSYNC with MS_INVALIDATE. As the original slots are in place during the merge, reads can continue while a merge takes place, until the original list must be deallocated.

Once deallocated, reads can now be directed to the newly created slot. The result is that the only cache which need be manually maintained for write-ordering purposes is the journal cache, which is an append-only cache similar to that implemented by the POSIX FILE C API, which is lightweight, and simple. All TSSLs that employ MMAP, even without additionally optimizing for serial writes like CHISL, typically avoid read overheads incurred by a user-space buffer cache. On the other hand, traditional DBMSes can not use mmap as provided by commodity operating systems. This is because standard kernels (e.g., Linux) currently have no portable method of pinning dirty pages in the system page cache. Without this, or some other write-ordering mechanism, traditional DBMSes that require overwrites (e.g., due to using B+-trees), will violate write-ordering and break their recoverability. Therefore, they are forced to rely on complex page cache implementations based on MALLOC or use complex kernel-communication mechanisms. TSSLs utilized in cloud-based data stores such as Cassandra, HBase, or CHISL never overwrite data during the serialization of a memtable to storage, and therefore need not pin buffer-cache pages, greatly simplifying these designs.

Exemplary Transactional Support

Figure 6:
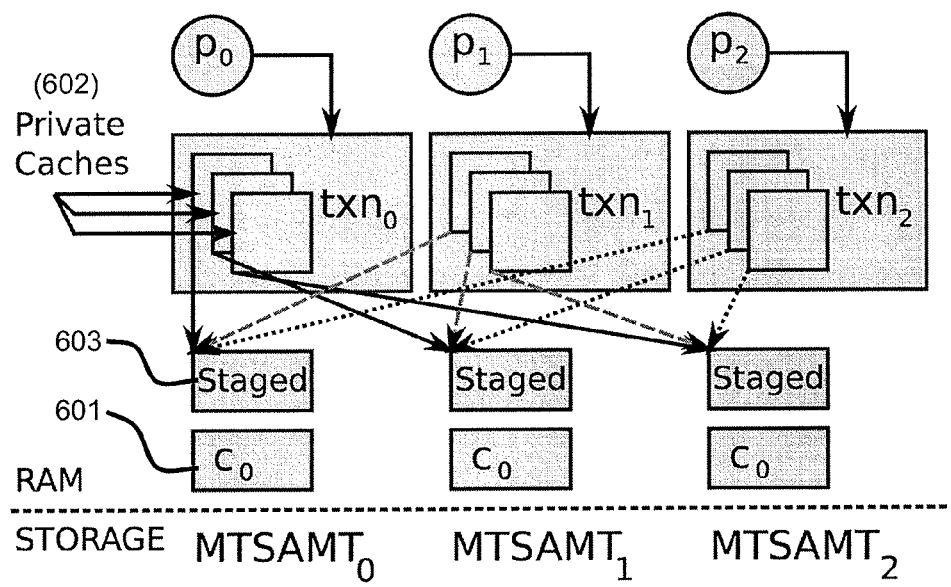
FIG. 6 shows three processes, $p_0 \ldots p_2$, each maintaining an ongoing transaction that has modified three SAMTs, according to an embodiment of the present application.

CHISL's optional transactional architecture permits for atomic durable insertions, batched insertions for higher insertion-throughput, and larger transactions that can be either asynchronous or durable. This lets the same TSSL architecture to be used in a cluster operating under either consistency model, if desired. MTSAMT's design and operation and its associated cache or memtable ($C_0$). As mentioned before, each MT-SAMT corresponds to a tree or column family in a cloud storage center. CHISL operates on multiple MTSAMTs to support row insertions across multiple column families, and more complex multi-operation transactions as required by stronger consistency models. Applications interact with the MTSAMTs through a transactional API: BEGIN, COMMIT_DURABLE, and COMMIT_ASYNC. CHISL's transaction manager (TM) manages all transactions for all threads. As shown in FIG. 6, the TM maintains a stacked scan cache called the staged cache on top of each tree's C0 (also a scan cache). When an application begins a transaction with BEGIN, the TM creates a handler for that transaction, and gives the application a reference to it. At any time, when a thread modifies a tree, a new scan cache is created if one does not already exist, and is stacked on top of that tree's staged cache. The new scan cache is placed in that transaction's handler. This new scan cache is called a private cache. In FIG. 6 we see three handlers, each in use by three separate threads P0 through P2. Each thread has modified each of the three trees (MTSAMT0 through MTSAMT2). Transactions managed by CHISL's TM are in one of three states:

(1) they are uncommitted and still exist only with the handler's private caches;
(2) they are committed either durably or asynchronously and are in either the staged cache or C0 of the trees they effect; or
(3) they are entirely written to disk.

Transactions begin in state (1), move to state (2) when committed by a thread, and when CHISL performs a snapshot of the system, they move to state (3) and are atomically written to storage as part of taking the snapshot. Durable and asynchronous transactions can both be committed. We commit transactions durably by moving their transaction to state (2), and then scheduling and waiting for the system to perform a snapshot. While the system is writing a snapshot to storage, the staged cache is left unlocked so other threads can commit (similar to EXT3). A group commit of durable transactions occurs when multiple threads commit to the staged cache while the current snapshot is being written, and subsequently wait on the next snapshot together as a group before returning from COMMIT. Asynchronous transactions can safely commit to the staged cache and return immediately from COMMIT. After a snapshot the staged cache and the C0 cache swap roles: the staged cache becomes the C0 cache.

As shown in FIG. 6, the TM maintains a stacked cache called the staged cache on top of each pair type's $C_0$ 601. When an application begins a transaction with BEGIN, the TM creates a handler for that transaction and gives the application a reference to it. The first time the application reads or modifies a particular pair type, a new private cache txn0 602 is stacked on top of the staged cache 603 to hold those changes. Depending on whether the flusher is running or not, the application will commit differently. If the flusher is not running, the staged cache will be empty, and the TM will evict all the application's private caches into the corresponding $C_0$ directly. If the application is committing durably, it will initiate flush and wait for it to complete; otherwise it will return directly. If the flusher is running, the TM will evict the application's private caches into the staged cache. If the application is committing durably, it will enqueue itself onto the group commit queue. If it is committing asynchronously, it will return immediately.

CHISL's flush protocol ensures that all pair type caches are atomically written. Therefore, at the time of flush, the method determines whether the private caches of a transaction are wholly in the $C_0$ cache 601 or its staged cache 603 (or not). Using the $C_0$ cache 601 and the staged cache 603, it can be guaranteed that the private caches of a transaction exists in one of the $C_0$ cache 601 and the staged cache 603.

Exemplary Snapshot, Truncate, and Recovery Operations

CHISL manages blocks directly, not using separate files for each SSTable. A block allocator manages each storage device. Every block allocator uses a bitmap to track that blocks are in use. The block size used is 128 MB to prevent excessive fragmentation, but the operating system page cache still uses 4 KB pages for reads into the buffer cache. Each tree (column family) maintains a cluster of offsets and metadata information that points to the location of all SSTable block offsets, secondary index block offsets, and Bloom filter block offsets. This cluster may be called the header. When a snapshot is performed, all data referred to by all headers, including blocks containing SSTable information, and the bitmaps, are flushed to storage using MSYNC. Afterward, the append-only cache of the journal is flushed, recording all headers to the journal within a single atomic transaction.

During recovery, the most recent set of headers may be read back into RAM, and the state of the system at the time that header was committed to the journal may be recovered. Traditional TSSLs implement a limited transaction feature-set that only allows for atomic insertion. CHISL's architecture does not exclude distributed transactions and is as fast as traditional TSSLs like Cassandra or HBase, or a factor of 2 faster when all three systems use asynchronous commits. One feature of CHISL is that high-insertion throughput workloads that can tolerate partial durability (e.g., snapshotting every 3-5 seconds) need not write the majority of data into the journal. CHISL can avoid this write because if the $C_0$ cache evicts its memtable as an SSTable between snapshots, the cache will be marked clean, and only the header need be serialized to the journal, avoiding double writing. This design improves CHISL's performance.

3. Exemplary Implementations

It is to be understood that the present invention may be implemented in various forms of hardware, software, firmware, special purpose processors, or a combination thereof. In one embodiment, the present invention may be implemented in software as an application program tangibly embodied on a program storage device. The application program may be uploaded to, and executed by, a machine comprising any suitable architecture.

According to an embodiment of the present invention, a computer system for tiered indexing can comprise, inter alia, a central processing unit (CPU), a memory and an I/O interface. The computer system is generally coupled through the I/O interface to a display and various input devices such as a mouse and keyboard. The support circuits can include circuits such as cache, power supplies, clock circuits, and a communications bus. The memory can include random access memory (RAM), read only memory (ROM), disk drive, tape drive, etc., or a combination thereof. Embodiments of the present disclosure can be implemented as a routine that is stored in memory and executed by the CPU to process the signal from the signal source. As such, the computer system is a general purpose computer system that becomes a specific purpose computer system when executing the routine of the present invention.

The computer platform also includes an operating system and micro instruction code. The various processes and functions described herein may either be part of the micro instruction code or part of the application program (or a combination thereof) which is executed via the operating system. In addition, various other peripheral devices may be connected to the computer platform such as an additional data storage device and a printing device.

It is to be further understood that, because some of the constituent system components and method steps depicted in the accompanying figures may be implemented in software, the actual connections between the system components (or the process steps) may differ depending upon the manner in which the present invention is programmed. Given the teachings of the present invention provided herein, one of ordinary skill in the related art will be able to contemplate these and similar implementations or configurations of the present invention.

The invention claimed is:

1. A method of storing data as a plurality of key-value pairs in a multi-tier storage system, the system comprising at least one lower-latency non-volatile memory storage device and at least one higher-latency non-volatile memory storage device, the method comprising:
generating a first zone manager for managing a first partition of storage of a first non-volatile memory device among the lower-latency non-volatile memory storage devices to generate a tier of the multi-tier storage system;
generating a second zone manager for managing a second partition of storage of a second non-volatile memory device among the higher-latency non-volatile memory storage devices to generate another tier of the multi-tier storage system;
allocating, from the first zone manager, bytes pointed at by a more frequently accessed sub-list among all the key-value pairs in a key-value relation;
allocating, from the second zone manager, bytes pointed at by a less frequently accessed sub-list among all the key-value pairs in the key-value relation;
allocating bytes from the first zone manager for storing meta-data, where the meta-data comprises at least one association of the key-value relation with an array of pointers to sub-lists belonging to the relation, wherein each sub-list includes at least one pointer to bytes allocated for sorted key-value pairs comprising the corresponding sublist,
wherein each partition comprises at least one block of a given size, and
wherein the system maintains a hierarchy structure in one of the tiers that stores the key-value relation and enables the key-value pairs to be stored in any one of the tiers.

2. The method of claim 1, further comprising storing in one of the sub-lists a pointer to a secondary index and a pointer to bytes for data of the sorted list, said secondary index stores an index to the sorted list stored in bytes pointed at by this sub-list.

3. The method of claim 2, wherein the storing comprises:
allocating bytes from at least one of the zone managers for storing a sorted list of key-offset pairs or secondary index pairs;
dividing the sorted list being indexed into a set of finite ranges of key-value pairs; and
storing a secondary index pair to indicate the beginning of each range of key-value pairs stored in the list being indexed.

4. The method of claim 3, wherein the secondary index pair is a key and a value where the key is equivalent to the key of a first tuple in the range being indicated and the value of the offset of the first tuple in the range being indicated.

5. The method of claim 1, the structure comprising a compact negative cache in the first non-volatile memory device for at least one of the sublists in the second non-volatile memory device.

6. The method of claim 5, wherein the compact negative cache is a Bloom Filter.

7. The method of claim 1, wherein at least one of the key-value pairs is a variable length key-value pair.

8. The method of claim 1, the structure comprising a compact negative cache in the second non-volatile memory device for each sub-list in the second non-volatile memory device, and then transferring the structure from the second non-volatile memory device to the first non-volatile memory device.

9. The method of claim 8, wherein the compact negative cache is a Bloom Filter.

10. The method of claim 1, wherein the system further comprises a cache that stores one or more of the frequently used sublists from one or more of the tiers, wherein a storage device used for the cache has a lower latency than the at least one lower-latency non-volatile memory storage device for sequential or random access.

11. The method of claim 10, wherein the cache is one of a volatile memory or a non-volatile memory.

12. The method of claim 1, wherein at least one of the sublists is stored using a red-black tree.

13. The method of claim 1, wherein at least one of the sublists is stored using a B-tree data structure.

14. The method of claim 1, wherein at least one of the sublists is stored using an R-COLA data structure.

15. The method of claim 1, wherein at least one of the sublists is stored using a SAMT data structure.

16. The method of claim 1, where the allocating performed by at least one of the zone managers is with respect to bytes at multiple offsets.

17. The method of claim 1, where at least one of the sub-lists contains one or more key-value pairs indicating a deleted item.

18. The method of claim 1 where at least one of the sub-lists contains one or more key-value pairs indicating an updated item.

19. The method of claim 1, further comprising compacting a group of the sub-lists in one of the tiers into a fewer number of sub-lists according to a merging method.

20. The method of claim 19, further comprising reclaiming space resulting from the compacting from the corresponding zone manager.

21. The method of claim 20, further comprising transferring another group of the sub-lists into the reclaimed space.

* * * * *